United States Patent [19]
Ishigaki et al.

[11] Patent Number: 5,973,181
[45] Date of Patent: Oct. 26, 1999

[54] POLYFUNCTIONAL PEROXIDES, VINYL MONOMER POLYMERIZATION INITIATORS COMPRISING THE SAME AND PROCESS FOR POLYMERIZING VINYL MONOMERS EMPLOYING THE SAME

[76] Inventors: Hideyo Ishigaki, 19, Aza-Uchikoshi, Ohaza-Yataka Agui-cho, Chita-gun, Aichi-ken; Yasumasa Watanabe, 19, Aoyama-cho 4-chome, Handa-shi, Aichi-ken 475; Tomomi Satou, 56-7, Mizubuka, Arao-cho, Tokai-shi, Aichi-ken 476, all of Japan

[21] Appl. No.: 08/999,359

[22] Filed: Dec. 29, 1997

[30] Foreign Application Priority Data

Sep. 24, 1997 [JP] Japan ..................... 9-259072

[51] Int. Cl.⁶ .................. C08F 4/36; C08F 4/38
[52] U.S. Cl. ............ 558/263; 558/264; 558/267; 526/230.5
[58] Field of Search ................ 558/263, 264, 558/267; 526/230.5

[56] References Cited

U.S. PATENT DOCUMENTS

| | | |
|---|---|---|
| 3,652,631 | 3/1972 | Stevens et al. |
| 3,963,673 | 6/1976 | D'Angelo et al. ............ 558/263 |
| 4,136,105 | 1/1979 | Sanchez . |
| 5,455,321 | 10/1995 | Cummings et al. |
| 5,548,046 | 8/1996 | Sanchez .............. 526/230.5 |
| 5,760,149 | 6/1998 | Sanchez et al. .......... 558/263 |

FOREIGN PATENT DOCUMENTS

| | | |
|---|---|---|
| 40-19013 | 8/1965 | Japan . |
| 58-76405 | 5/1983 | Japan . |
| 61-231005 | 10/1986 | Japan . |
| 049969 | 11/1966 | United Kingdom . |
| 98/07684 | 2/1998 | WIPO . |

*Primary Examiner*—Tae Yoon

[57] ABSTRACT

The novel polyfunctional peroxides are compounds represented by the following general formula (1):

$$R^1\text{---}CX_3 \quad (1)$$

wherein $R^1$ represents a linear alkyl group having 1 to 3 carbon atoms; and X represents a group:

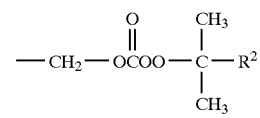

(wherein $R^2$ represents a linear or branched alkyl group having 1 to 5 carbon atoms).

Such polyfunctional peroxides include 1,1,1-tris(t-butylperoxycarbonyloxymethyl)propane and the like. The polymerization initiators for vinyl monomers comprise such polyfunctional peroxides. In the process for polymerizing vinyl monomers, a vinyl monomer is polymerized employing such polyfunctional peroxide at 60 to 160° C.

3 Claims, No Drawings

POLYFUNCTIONAL PEROXIDES, VINYL MONOMER POLYMERIZATION INITIATORS COMPRISING THE SAME AND PROCESS FOR POLYMERIZING VINYL MONOMERS EMPLOYING THE SAME

BACKGROUND OF THE INVENTION

1. Field of the Invention

The present invention relates to a novel polyfunctional peroxide to be utilized as a polymerization initiator for a vinyl monomer, a curing agent and a crosslinking agent for a polymer, a polymerization initiator comprising the same and a process for polymerizing a vinyl monomer employing the same.

2. Description of the Related Art

Polyfunctional peroxides having a plurality of peroxy bonds have conventionally been employed as polymerization initiators, when high molecular weight vinyl polymers are to be obtained by subjecting vinyl monomers to bulk polymerization or suspension polymerization.

Various kinds of compounds are so far known as such polyfunctional peroxides. For example, U.K. Patent No. 1049969 discloses 1,1,4,4-tetra(t-butylperoxy)cyclohexane. Japanese Patent Publication No. Sho 40-19013 discloses 2,2-bis (4,4-di(t-butylperoxy)cyclohexyl)propane. Japanese Patent Publication No. Sho 58-56561 discloses tri(t-butylperoxy)triazine. Japanese Patent Publication No. Hei 1-30844 discloses tri(t-butylperoxy)trimellitate.

However, these conventional polymerization initiators have low polymerization initiation efficiency, so that they have a low probability that all of the peroxy bonds which are present in each molecule act effectively as the polymerization initiator. Accordingly, the conventional polymerization initiators substantially act as the polyfunctional initiators at low rates.

More specifically, polymerization mechanism resorting to a polyfunctional peroxide is supposed to operate usually as follows. First, radicals formed by initial cleavage of some of the peroxy bonds in the polyfunctional peroxide are added to the monomer to initiate polymerization thereof. Thus, a polymer containing peroxy groups is formed. The polymerization initiation efficiency at this initial stage is substantially the same as those of the conventional monofunctional peroxides.

Next, the peroxide moieties in the polymer are decomposed to form polymer radicals, which initiate another polymerization to form a high molecular weight polymer or a branched polymer. However, the conventional polyfunctional peroxides involve a problem that the polymer radicals serving as the polymerization initiator in the second step have low polymerization initiation efficiency. Accordingly, polyfunctional polymerization initiators having higher polymerization initiation efficiency are in demand.

SUMMARY OF THE INVENTION

It is an objective of the present invention to provide a novel polyfunctional peroxide useful as a polymerization initiator etc.

It is another objective of the invention to provide a polymerization initiator for a vinyl monomer, which has peroxy bonds functioning effectively as the polymerization initiator and also has high polymerization initiation efficiency.

It is another objective of the invention to provide a process for polymerizing a vinyl monomer, which can give a high molecular weight vinyl polymer in a high yield, the polymer having a low melt viscosity and excellent molding properties because of its branched structure.

The novel peroxide according to the present invention, in order to attain the objectives described above, is represented by the following general formula (1):

wherein $R^1$ represents a linear alkyl group having 1 to 3 carbon atoms; and X represents a group:

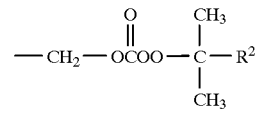

(wherein $R^2$ represents a linear or branched alkyl group having 1 to 5 carbon atoms).

Meanwhile, another novel polyfunctional peroxide is represented by the following general formula (2):

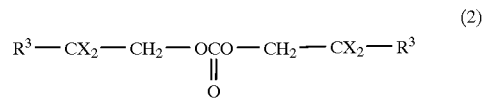

wherein $R^3$ represents a linear alkyl group having 1 to 3 carbon atoms; and X represents a group:

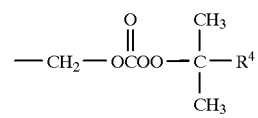

(wherein $R^4$ represents a linear or branched alkyl group having 1 to 5 carbon atoms).

The features of the present invention that are believed to be novel are set forth with particularity in the appended claims.

The invention, together with the objects and advantages thereof, may best be understood by reference to the following description of the presently preferred embodiments.

DETAILED DESCRIPTION OF THE PREFERRED EMBODIMENTS

Embodiments of the present invention will be described in detail.

The novel polyfunctional peroxide according to the present invention is a compound represented by the following general formula (1):

wherein $R^1$ represents a linear alkyl group having 1 to 3 carbon atoms; and X represents a group:

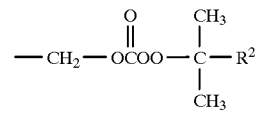

(wherein $R^2$ represents a linear or branched alkyl group having 1 to 5 carbon atoms).

The polyfunctional peroxide represented by the general formula (1) typically includes, for example, 1,1,1-tris(t-butylperoxycarbonyloxymethyl)propane, 1,1,1-tris(1,1-dimethylpropylperoxycarbonyloxymethyl)propane, 1,1,1-tris(1,1-dimethylbutylperoxycarbonyloxymethyl)propane, 1,1,1-tris(1,1,2-trimethylpropylperoxycarbonyloxymethyl) propane, 1,1,1-tris (1,1,3,3-tetramethylbutylperoxycarbonyloxymethyl)propane, 1,1,1-tris(cumylperoxycarbonyloxymethyl)propane, 1,1,1-tris (t-butylperoxycarbonyloxymethyl)ethane, 1,1,1-tris(1,1-dimethylbutylperoxycarbonyloxymethyl)ethane, 1,1,1-tris (t-butylperoxycarbonyloxymethyl)butane and 1,1,1-tris(1,1-dimethylbutylperoxycarbonyloxymethyl)butane.

More preferred among these polyfunctional peroxides are 1,1,1-tris(t-butylperoxycarbonyloxymethyl)propane, 1,1,1-tris (1,1-dimethylbutylperoxycarbonyloxymethyl)propane or 1,1,1-tris(1,1,3,3-tetramethylbutylperoxycarbonyloxymethyl)propane. That is, in the more preferred polyfunctional peroxides having the general formula (1), $R^1$ represents an ethyl group, and $R^2$ contained in X represents a methyl group, a n-propyl group or a branched alkyl group having 5 carbon atoms. The reason is that, in such polyfunctional peroxides, the peroxy bonds in each molecule have high polymerization initiation efficiency to exhibit excellent function as the polymerization initiator.

These polyfunctional peroxides are prepared according to the following method: a corresponding hydroperoxide is reacted with a polyfunctional chloroformate which is a starting material of the peroxide having the general formula (1) in the presence of an alkali.

The corresponding hydroperoxide includes, for example, t-butyl hydroperoxide, 1,1-dimethylpropyl hydroperoxide, 1,1-dimethylbutyl hydroperoxide, 1,1,2-trimethylpropyl hydroperoxide, 1,1,3,3-tetramethylbutyl hydroperoxide and cumene hydroperoxide.

As the polyfunctional chloroformate, the starting material of the peroxide having the formula (1), there may be employed, for example, trimethylolpropane trischloroformate or trimethylolethane trischloroformate.

The alkali employable in the reaction includes, for example, sodium hydroxide, potassium hydroxide, sodium carbonate, sodium hydrogencarbonate, calcium hydroxide, barium hydroxide, pyridine and triethylamine. Among others, sodium hydroxide and potassium hydroxide are more preferred, since they can improve the yield of products.

When a polyfunctional peroxide is prepared, a solvent such as of paraffinic hydrocarbons and aromatic hydrocarbons may also be employed. The reaction is usually carried out at a temperature of 0 to 50° C., preferably at 5 to 35° C. If the reaction temperature is lower than 0° C., the reaction does not take place sufficiently; whereas at a temperature of higher than 50° C., control of the reaction tends to be difficult, because the reaction takes place suddenly.

Another novel polyfunctional peroxide according to the present invention is a compound represented by the following general formula (2):

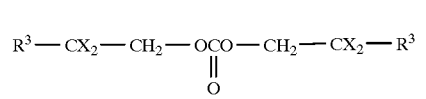

(2)

wherein $R^3$ represents a linear alkyl group having 1 to 3 carbon atoms; and X represents a group:

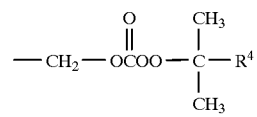

(wherein $R^4$ represents a linear or branched alkyl group having 1 to 5 carbon atoms).

The polyfunctional peroxide represented by the general formula (2) typically includes, for example, di(2,2-bis (t-butylperoxycarbonyloxymethyl)butyl) carbonate, di(2,2-bis (1,1-dimethylpropylperoxycarbonyloxymethyl) butyl) carbonate, di(2,2-bis (1,1-dimethylbutylperoxycarbonyloxymethyl)butyl) carbonate, di(2,2-bis(1,1, 2-trimethylpropylperoxycarbonyloxymethyl) butyl) carbonate, di(2,2-bis(1,1,3,3-tetramethylbutylperoxycarbonyloxymethyl)butyl) carbonate, di(2,2-bis(cumylperoxycarbonyloxymethyl) butyl) carbonate, di(2,2-bis (t-butylperoxycarbonyloxymethyl)propyl carbonate and di(2,2-bis(1,1-dimethylbutylperoxycarbonyloxymethyl) propyl) carbonate.

More preferred among these polyfunctional peroxides are di(2,2-bis(t-butylperoxycarbonyloxymethyl)butyl) carbonate and di(2,2-bis (1,1-dimethylbutylperoxycarbonyloxymethyl)butyl) carbonate. That is, in the preferred polyfunctional peroxides having the general formula (2), $R^3$ represents an ethyl group; and $R^4$ contained in X represents a methyl group or a n-propyl group. The reason is that the peroxy bonds in each molecule have high polymerization initiation efficiency to exhibit excellent function as the polymerization initiator.

These polyfunctional peroxides are prepared according to the following method: a corresponding hydroperoxide is reacted with a polyfunctional chloroformate which is a starting material of the peroxide having the general formula (2) in the presence of an alkali.

The corresponding hydroperoxide includes the hydroperoxides as the starting materials of the peroxides having the general formula (1) exemplified above.

Meanwhile, as the polyfunctional chloroformate, the starting material of the polyfunctional peroxide having the general formula (2), there may be employed, for example, di(2,2-bis(chlorocarbonyloxymethyl)butyl) carbonate and di(2,2-bis(chlorocarbonyloxymethyl)propyl) carbonate. These polyfunctional chloroformates can be obtained as major components from a polyfunctional chloroformate which is a starting material of the polyfunctional peroxide having the general formula (1) and a corresponding polyfunctional alcohol under control of reaction conditions.

Accordingly, the starting material of the polyfunctional peroxide having the general formula (1) and that of the polyfunctional peroxide having the general formula (2) are of the same polyfunctional alcohols. The polyfunctional alcohols include, for example, trimethylolpropane and trimethylolethane.

The alkali employable in the preparation of the polyfunctional peroxide having the general formula (2) includes those as listed referring to the preparation of the polyfunctional peroxide having the general formula (1).

Further, the polyfunctional chloroformate which is a starting material of the polyfunctional peroxide having the general formula (2) may be contained in the polyfunctional chloroformate which is a starting material of the polyfunctional peroxide having the general formula (1). In this case, the resulting polyfunctional peroxide is a mixture of the polyfunctional peroxides of the general formula (1) and that of the general formula (2).

Next, the polymerization initiator according to the present invention is a novel peroxide represented by the general formula (1) or (2). As the polymerization initiator, at least one polyfunctional peroxide selected from these peroxides is usually employed. It is also possible here to employ a combination of the polyfunctional peroxide of the general formula (1) and that of the general formula (2). The effects of these polyfunctional peroxides (1) and (2) can be exhibited synergistically depending on the combination.

As the polymerization initiator, other polymerization initiators may be employed in addition to the polyfunctional peroxide of the general formula (1) or (2). When another polymerization initiator is employed, the polymerization rate can be increased. In this case, the molecular weight of the resulting polymer is reduced. Further, a chain transfer agent may also be employed additionally. When a chain transfer agent is employed, the molecular weight of the resulting polymer and polymerization rate can be adjusted.

A vinyl monomer is polymerized by employing the polymerization initiator. described above. The vinyl monomer employable in the polymerization reaction includes, for example, styrene monomers such as styrene, α-methylstyrene and vinyltoluene; acrylic monomers such as acrylic acid, methyl acrylate, ethyl acrylate, propyl acrylate, butyl acrylate, octyl acrylate, lauryl acrylate, 2-hydroxyethyl acrylate and 2-hydroxypropyl acrylate; methacrylic monomers such as methacrylic acid, methyl methacrylate, ethyl methacrylate, propyl methacrylate, butyl methacrylate, octyl methacrylate, lauryl methacrylate, 2-hydroxyethyl methacrylate and 2-hydroxypropyl methacrylate; and fumaric acid esters, maleic acid esters, acrylonitrile, N-phenylmaleimide, vinyl chloride, vinyl acetate and vinylidene chloride.

The vinyl monomer preferably includes, for example, styrene, α-methylstyrene, acrylonitrile, N-phenylmaleimide, methyl methacrylate and butyl methacrylate. These monomers may be employed singly or as a suitable combination of two or more of them. The monomer combinations may be exemplified by styrene and methyl methacrylate; styrene and butyl acrylate; styrene and acrylonitrile; styrene and N-phenylmaleimide; styrene and α-methylstyrene; and α-methylstyrene and acrylonitrile.

It is also possible to employ a solution of a rubber such as of polybutadiene, styrene-butadiene copolymer, ethylene-propylene copolymer or ethylene-propylene-diene copolymer in such vinyl monomer.

Resins to be obtained from the rubbery components and the monomers include, for example, high-impact polystyrene resins (HIPS) consisting of styrene and a butadiene-containing rubber; and high-impact styrene-acrylonitrile resins (ABS resins) consisting of styrene, acrylonitrile and a butadiene-containing rubber.

Other polymerization initiators employable additionally include, for example, t-butylperoxyisopropyl monocarbonate, 1,1-dimethylbutylperoxyisopropyl monocarbonate, t-butylperoxy-2-ethylhexyl monocarbonate, 2,2-bis(4,4-di(t-butylperoxy)cyclohexyl) propane, di-t-butyl peroxide, t-butyl peroxybenzoate and 1,1-dimethylbutyl peroxybenzoate.

The chain transfer agent employable additionally includes, for example, n-octylmercaptan, n-dodecylmercaptan, t-dodecylmercaptan, 3-mercaptopropionic acid and an α-methylstyrene dimer.

The polymerization initiator is employed in the polymerization reaction preferably in an amount of 0.001 to 5 parts by weight, more preferably in an amount of 0.01 to 1 part by weight in terms of purity per 100 parts by weight of the vinyl monomer employed. If the polymerization initiator is used in an amount of less than 0.001 part by weight, the polymerization rate will be reduced; whereas if it is used in an amount of more than 5 parts by weight, the polymerization rate is increased, and control of the polymerization rate tends to be difficult.

Next, referring to the process for polymerizing a vinyl monomer according to the present invention, a vinyl monomer is polymerized at a temperature of 60 to 160° C. employing as the polymerization initiator at least one compound selected from the polyfunctional peroxides represented by the general formula (1) or (2). As a method of polymerizing the vinyl monomer, there may be employed bulk polymerization, solution polymerization or suspension polymerization, and it is also possible to employ a combination of such polymerization methods. Further, batchwise polymerization or continuous polymerization may also be employed. In the bulk polymerization and suspension polymerization of these polymerization methods, vinyl monomers are polymerized under substantially the same conditions, except for the presence and absence of water.

The polymerization initiator is employed preferably in an amount of 0.001 to 1 part by weight in bulk polymerization, in an amount of 0.01 to 2 parts by weight in suspension polymerization, and in an amount of 0.01 to 5 parts by weight in solution polymerization, per 100 parts by weight of vinyl monomers employed.

The polymerization temperature is 60 to 160° C. as described above, preferably 80 to 150° C. If the polymerization temperature is lower than 60° C., not only the polymerization rate will be reduced, but also all of the peroxy bonds in the polymerization initiator do not decompose before completion of polymerization, and thus the initiator does not function as a polyfunctional polymerization initiator. Meanwhile, at a temperature higher than 160° C., the polymerization rate is increased to make adjustment of polymerization rate difficult. Besides, a large amount of polymerization initiating radicals are formed in a very short time. Thus, side reactions between the radicals such as primary radical termination occur to lower the polymerization initiation efficiency, consequently.

The solvent employable in solution polymerization includes aromatic hydrocarbons such as ethylbenzene, xylene and toluene; ketones such as acetone, methyl ethyl ketone, methyl isobutyl ketone and cyclohexanone; alcohols such as isobutanol, n-butanol, ethyl cellosolve and cyclohexyl alcohol; esters such as methyl acetate and n-butyl acetate; and ethers. While the amount of such solvent employed is adjusted depending on the configuration, performance, etc. of the polymer, it is preferably 1 to 80% by weight, more preferably 5 to 50% by weight of the entire polymer mixture.

As detailed above, the following effects are exhibited according to the embodiments of the present invention.

(1) The novel polyfunctional peroxide represented by the general formula (1) or (2) is useful as a polymerization initiator and the like.

(2) In the polymerization initiator for vinyl polymers of the embodiment, the peroxy bonds in the polyfunctional peroxide represented by the general formula (1) or (2) function effectively as the polymerization initiator, so that the polyfunctional peroxide has high polymerization initiation efficiency.

(3) In the polymerization initiator for vinyl monomers in the embodiment, radicals to be formed in the latter polymerization step where the peroxy bonds in the peroxy bond-containing polymer are cleaved act effectively without loosing their function to maintain high polymerization initiation efficiency. Accordingly, a branched polymer can be formed effectively.

(4) According to the process for polymerizing a vinyl monomer, a high molecular weight polymer can be obtained in a high yield, since the polyfunctional peroxide represented by the general formula (1) or (2) employed as the polymerization initiator has high polymerization initiation efficiency and high efficiency as the polyfunctional initiator.

(5) According to the process for polymerizing a vinyl monomer, a branched vinyl polymer can be obtained, since a polyfunctional peroxide represented by the general formula (1) or (2) is employed as the polymerization initiator.

(6) According to the process for polymerizing a vinyl monomer, since the resulting branched vinyl polymer has a melt flow index higher than those of linear polymers having equivalent molecular weights, the vinyl polymer has a low melt viscosity and excellent molding properties.

EXAMPLES

Next, the present invention will be described more specifically by way of examples and comparative examples. It should be noted here that abbreviations used in the following examples stand for the following compounds respectively:

TBPP: 1,1,1-tris(t-butylperoxycarbonyloxymethyl)propane
THPP: 1,1,1-tris(1,1-diemthylbutylperoxycarbonyloxymethyl)propane
TOPP: 1,1,1-tris (1,1,3,3-tetramethylbutylperoxycarbonyloxymethyl)propane
TBPD: di(2,2-bis(t-butylperoxycarbonyloxymethyl)butyl) carbonate
THPD: di-(2,2-bis(1,1-dimethylbuthylperoxycarbonyloxymethyl) butyl) carbonate
TBCH: 1,1,4,4-tetra(t-butylperoxy)cyclohexane
BBCP: 2,2-bis(4,4-di(t-butylperoxy)cyclohexylpropane
TBTA: tri(t-butylperoxy)triazine
TBTM: tri(t-butylperoxy)trimellitate.

Example 1

Synthesis of TBPP

To a 1000 ml four-necked flask equipped with a stirrer were introduced 96.5 g of a 98% trimethylolpropane trischloroformate and 225 g of toluene. While the temperature of the resulting mixture was maintained at 18° C. with stirring, a mixture of 219.0 g of a 30% aqueous potassium hydroxide solution and 152.6 g of a 70% aqueous t-butyl hydroperoxide solution was dropped thereto over 30 minutes, and a reaction was continued for 90 minutes in the same state. Subsequently, the organic layer was separated and washed twice with a 5% aqueous sodium hydroxide solution. The organic layer was further rinsed with water, dehydrated and filtered.

When the organic layer was treated as described above, 312 g of a liquid was obtained. The concentration of TBPP in the solution was found to be 36.7% by measuring the amount of active oxygen, and the yield of synthesis based on the starting material chloroformate was 79%. A portion of the solution was taken as a sample, and the toluene was removed therefrom to give a product having a purity of 99%. The product was then subjected to nuclear magnetic resonance spectrometry (H-NMR) to detect peaks: 0.94 ppm (3H), 1.54 ppm (2H), 4.21 ppm (6H) and 1.33 ppm (27H). Further, absorption bands corresponding to C=O were observed at 1794 cm$^{-1}$ and 1763 cm$^{-1}$ by means of infrared (IR) absorption spectrometry.

Elementary analysis of the product gave the following results: carbon (C): 52.44% (theoretical value for TBPP: 52.27%); hydrogen (H): 7.88% (theoretical value for TBPP: 7.94%); oxygen (O): 39.68% (theoretical value for TBPP: 39.79%). The found values of elementary analysis were very close to the theoretical values respectively. Based on these results, the product obtained was identified to be TBPP.

The TBPP thus obtained was further subjected to pyrolysis in benzene at a concentration of 0.01 mol/liter so as to measure the rate of pyrolysis. The 10-hour half life temperature (the temperature at which the amount of active oxygen decreases to 50% in 10 hours, which is hereinafter abbreviated as T10) was 101° C.

Example 2

Synthesis of THPP

A reaction was carried out in the same manner as in Example 1 except that 152.6 g of the 70% aqueous t-butyl hydroperoxide solution was replaced with 144.4 g of an aqueous 97% 1,1-dimethylbutyl hydroperoxide. After completion of the reaction, the organic layer was separated and washed with an aqueous sodium sulfite solution, followed by rinsing with water, dehydration and filtration, to give 332 g of a liquid. The concentration of THPP in the solution was found to be 40.5% by measuring the amount of active oxygen, and the yield of synthesis based on the starting material chloroformate was 79%.

A portion of the solution was taken as a sample, and the toluene was removed therefrom to give a product having a purity of 97%. The product was then subjected to nuclear magnetic resonance spectrometry (H-NMR) to detect peaks: 0.94 ppm (3H), 1.53 ppm (2H), 4.21 ppm (6H), 1.28 ppm (18H), 1.59 ppm (6H), 1.55 ppm (6H) and 0.92 ppm (9H). Further, absorption bands corresponding to C=O were observed at 1794 cm$^{-1}$ and 1763 cm$^{-1}$ by means of infrared (IR) absorption spectrometry.

Elementary analysis of the product gave the following results: carbon (C): 57.49% (theoretical value for THPP: 57.23%); hydrogen (H): 8.68% (theoretical value for THPP: 8.89%); oxygen (O): 33.83% (theoretical value for THPP: 33.88%). The found values of elementary analysis were very close to the theoretical values respectively. Based on these results, the product obtained was identified to be THPP.

T10 of the THPP thus obtained measured in benzene at a concentration of 0.01 mol/liter was 97° C.

Example 3

Synthesis of TOPP

A reaction was carried out in the same manner as in Example 2 except that 144.4 g of the 97% aqueous 1,1-dimethylbutyl hydroperoxide was replaced with 180.6 g of a 96% aqueous 1,1,3,3-tetramethylbutyl hydroperoxide to give 348 g of a liquid. The concentration of TOPP in the solution was found to be 43.2% by measuring the amount of active oxygen, and the yield of synthesis based on the starting material chloroformate was 77%.

A portion of the solution was taken as a sample, and the toluene was removed therefrom to give a product having a purity of 96%. The product was then subjected to nuclear magnetic resonance spectrometry (H-NMR) to detect peaks: 0.94 ppm (3H), 1.54 ppm (2H), 4.21 ppm (6H), 1.37 ppm (18H), 1.64 ppm (6H) and 1.03 ppm (27H). Further, absorption bands corresponding to C=O were observed at 1794 cm$^{-1}$ and 1763 cm$^{-1}$ by means of infrared (IR) absorption spectrometry.

Elementary analysis of the product gave the following results: carbon (C): 61.36% (theoretical value for TOPP: 60.90%); hydrogen (H): 9.58% (theoretical value for TOPP: 9.60%); oxygen (O): 29.06% (theoretical value for TOPP: 29.50%). The found values of elementary analysis were very close to the theoretical values respectively. Based on these results, the product obtained was identified to be TOPP.

T10 of the TOPP thus obtained measured in benzene at a concentration of 0.01 mol/liter was 93° C.

Example 4
Synthesis of TBPD

A reaction was carried out in the same manner as in Example 1 except that 96.5 g of the 98% trimethylolpropane trischloroformate was replaced with 122.4 g of a 90% di(2,2-bis (chlorocarbonyloxymethyl)butyl) carbonate. The rest (10%) of the chloroformate solution was trimethylolpropane trischloroformate. Thus, 326 g of a liquid was obtained. The concentration of TBPD in the solution was found to be 39.3% by measuring the amount of active oxygen, and the yield of synthesis based on the starting material carbonate was 75%.

The solution was treated to give a product having a purity of 93%, and then the product was subjected to nuclear magnetic resonance spectrometry (H-NMR) to detect peaks: 0.94 ppm (6H), 1.54 ppm (4H), 4.23 ppm (8H), 4.21 ppm (4H) and 1.33 ppm (36H). Further, absorption bands corresponding to C=O were observed at 1794 cm$^{-1}$ and 1763 cm$^{-1}$ by means of infrared (IR) absorption spectrometry.

Elementary analysis of the product gave the following results: carbon (C): 52.01% (theoretical value for TBPD: 52.23%); hydrogen (H): 7.64% (theoretical value for TBPD: 7.70%); oxygen (O): 40.35% (theoretical value for TBPD: 40.07%). The found values of elementary analysis were very close to the theoretical values respectively. Based on these results, the product obtained was identified to be TBPD.

T10 of the TBPD thus obtained measured in benzene at a concentration of 0.01 mol/liter was 103° C.

Example 5
Synthesis of THPD

A reaction was carried out in the same manner as in Example 4 except that 152.6 g of the 70% aqueous t-butyl hydroperoxide solution was replaced with 144.4 g of a 97% 1,1-dimethylbutyl hydroperoxide to give 353 g of a liquid. The concentration of THPD in the solution was found to be 43.8% by measuring the amount of active oxygen, and the yield of synthesis based on the starting material carbonate was 75%.

The solution was treated to give a product having a purity of 93%, and then the product was subjected to nuclear magnetic resonance spectrometry (H-NMR) to detect peaks: 0.94 ppm (6H), 1.53 ppm (4H), 4.22 ppm (8H), 4.20 ppm (4H), 1.26 ppm (24H), 1.59 ppm (8H), 1,55 ppm (8H) and 0.91 ppm (12H). Further, absorption bands corresponding to C=O were observed at 1794 cm$^{-1}$ and 1763 cm$^{-1}$ by means of infrared (IR) absorption spectrometry.

Elementary analysis of the product gave the following results: carbon (C): 57.01% (theoretical value for THPD: 56.53%); hydrogen (H): 8.44% (theoretical value for THPD: 8.56%); oxygen (O): 34.55% (theoretical value for THPD: 34.91%). The found values of elementary analysis were very close to the theoretical values respectively. Based on these results, the product obtained was identified to be THPD.

T10 of the THPD thus obtained measured in benzene at a concentration of 0.01 mol/liter was 98° C.

Example 6
Bulk Polymerization of Styrene

To a glass ampoule having an inside diameter of 4 mm and a length of 300 mm was introduced 2 ml of styrene containing 322 ppm (0.002 mol/kg in terms of —OO— bonds) of TBPP in terms of purity (the same shall apply hereinafter) dissolved therein. After the gas in the ampoule was replaced with nitrogen, the ampoule was sealed and immersed in a thermostatic bath at 120° C. to effect bulk polymerization for 10 hours. After completion of polymerization, polymer conversion rate was found by determining the amount of residual styrene by means of gas chromatography. Further, number average molecular weight (Mn) and weight average molecular weight (Mw) of the resulting polymer were determined by means of gel permeation chromatography (GPC). Results are as shown in Table 1.

Examples 7 to 9

Tests were carried out in the same manner as in Example 6, except that TBPP employed in Example 6 was replaced with polyfunctional peroxides (0.002 mol/kg in terms of —OO— bonds) as listed in Table 1 respectively. Results are as shown in Table 1.

Example 10

A test was carried out in the same manner as in Example 6, except that half of TBPP (0.001 mol/kg in terms of —OO— bonds) employed in Example 6 was replaced with TBPD. Results are as shown in Table 1.

Comparative Examples 1 to 4

Tests were carried out in the same manner as in Example 6, except that TBPP employed in Example 6 was replaced with conventional polyfunctional peroxides (0.002 mol/kg in terms of —OO— bonds) as listed in Table 1 respectively. Results are as shown in Table 1.

TABLE 1

| Example/ Comp. Example | Polymerization initiator | Loading (ppm) | Polymerization temp. (° C.) | Polymerization time (h) | Polymer conversion rate (%) | Mn | Mw |
| --- | --- | --- | --- | --- | --- | --- | --- |
| Example 6 | TBPP | 322 | 120 | 10 | 99.5 | 253000 | 559000 |
| Example 7 | THPP | 378 | 120 | 10 | 98.5 | 256000 | 553000 |
| Example 8 | TOPP | 434 | 120 | 10 | 98.7 | 254000 | 532000 |
| Example 9 | TBPD | 379 | 120 | 10 | 99.4 | 253000 | 629000 |
| Example 10 | TBPP | 161 | 120 | 10 | 99.5 | 254000 | 601000 |
|  | TBPD | 190 |  |  |  |  |  |
| Comp. Ex. 1 | TBCH | 218 | 120 | 10 | 85.1 | 182000 | 380000 |
| Comp. Ex. 2 | BBCP | 280 | 120 | 10 | 86.9 | 237000 | 490000 |
| Comp. Ex. 3 | TBTA | 230 | 120 | 10 | 87.5 | 209000 | 416000 |
| Comp. Ex. 4 | TBTM | 236 | 120 | 10 | 88.8 | 224000 | 428000 |

As can be understood from Examples 6 to 10 and Comparative Examples 1 to 4 shown in Table 1, in the cases where the polyfunctional peroxides of Examples 6 to 10 were employed as polymerization initiators, the polymer conversion rates are high compared with the cases where the conventional polyfunctional peroxides were employed in equimolar amounts in terms of peroxy bonds (—OO— bonds), and high molecular weight compounds were obtained. Such results are surmised to be brought about by the plurality of peroxy bonds contained in the polyfunctional peroxide in each Example which acted with high polymerization initiation efficiency as the polymerization initiator.

Example 11
Copolymerization of Styrene and N-phenylmaleimide

A reaction was carried out in the same manner as in Example 6, except that styrene employed in Example 6 was replaced with styrene/N-phenylmaleimide=85:15 in terms of weight ratio. As a result, polymer conversion rate, Mn and Mw were 68.6%, 310000 and 601000 respectively. The polymer thus formed was colorless.

Comparative Example 5

A reaction was carried out in the same manner as in Example 11, except that TBPP employed in Example 11 was replaced with 280 ppm of BBCP as a conventional polyfunctional peroxide. As a result, polymer conversion rate, Mn and Mw were 66.0%, 282000 and 559000 respectively. The results of Example 11 and Comparative Example 5 demonstrated that the use of styrene and N-phenylmaleimide also exhibits an effect of achieving a high polymer conversion rate and giving a high molecular weight polymer.

Example 12
Copolymerization of α-methylstyrene and Acrylonitrile

A reaction was carried out in the same manner as in Example 6, except that styrene employed in Example 6 was replaced with α-methylstyrene/acrylonitrile=85:15 in terms of weight ratio and that 1608 ppm of TBPP was employed. As a result, polymer conversion rate, Mn and Mw were 68.6%, 310000 and 601000 respectively. The polymer thus formed was colorless.

Comparative Example 6

A reaction was carried out in the same manner as in Example 12, except that TBPP employed in Example 12 was replaced with 1402 ppm of BBCP as a conventional polyfunctional peroxide. As a result, polymer conversion rate, Mn and Mw were 66.0%, 282000 and 559000 respectively.

The results of Example 12 and Comparative Example 6 demonstrated that the use of α-methylstyrene and acrylonitrile has the same effect as described above.

Example 13
Copolymerization of Styrene and Butyl Acrylate

A reaction was carried out in the same manner as in Example 6, except that styrene employed in Example 6 was replaced with styrene/butyl acrylate=80:20 in terms of weight ratio and that 1608 ppm of TBPP was employed. As a result, polymer conversion rate, Mn and Mw were 99.1%, 236000 and 515000 respectively.

Comparative Example 7

A reaction was carried out in the same manner as in Example 13, except that TBPP employed in Example 13 was replaced with 1402 ppm of BBCP. As a result, polymer conversion rate, Mn and Mw were 98.8%, 211000 and 448000 respectively.

The results of Example 13 and Comparative Example 7 demonstrated that the use of styrene and butyl acrylate has the same effect as described above.

Example 14
Suspension Polymerization of Styrene

To a 1000 ml-capacity stainless steel autoclave were introduced 400 ml of a deionized water, 8 g of tricalcium phosphate and 0.1 g of sodium dodecylbenzenesulfonate, followed by addition of 200 g of styrene and 0.0642 g of TBPP (in terms of purity) thereto.

The gas present in the vacant space of the autoclave was replaced fully with a nitrogen gas, and then the autoclave was hermetically sealed. The resulting mixture was heated to 100° C. with stirring to effect polymerization for 3 hours. The mixture was further heated to 130° C. over 5 hours and then polymerized at the same temperature for 2 hours. After completion of polymerization, the resulting mixture was cooled, filtered, washed with hydrochloric acid, rinsed with water and then dried to give 197 g of a polymer. The residual vinyl monomer was analyzed by means of gas chromatography (GLC) to be 0.1%. The polymer thus obtained had Mn of 186000 and Mw of 359000. Melt flow index (IM) (expressing flowability of a melt) of the polymer was measured in accordance with JIS K-6870. The polymer was found to have an MI of 6.4 (g/10 min).

Comparative Example 8

The same autoclave as employed in Example 14 was used, and the same compounds as employed in Example 14 were introduced thereto, except that 0.0642 g of TBPP was replaced with 0.0566 g of TBTM (in terms of purity). The resulting mixture was heated to 110° C. with stirring to effect polymerization for 3 hours. The mixture was further heated to 140° C. over 5 hours and then polymerized at the same temperature for 2 hours. After completion of polymerization, the resulting mixture was cooled, filtered, washed with hydrochloric acid, rinsed with water and then dried to give 198 g of a polymer. The polymer thus obtained had Mn of 177000 and Mw of 354000. Melt flow index (IM) of the polymer was 4.3 (g/10 min).

In Example 14 and Comparative Example 8, polymers having substantially the same molecular weights were prepared by adjusting the amount of polymerization initiator employed and the polymerization temperature, and melt flow indices of the polymers were measured. The result of Example 14 demonstrated that the polymer has a melt flow index value of greater than that in Comparative Example 8 and has excellent flowability in molding. This shows that the polymer obtained has a branched structure.

Example 15
Preparation of HIPS

To a 2000 ml-capacity four-necked flask equipped with a stirrer, a condenser and a nitrogen introducing pipe were introduced 1500 g of a solution of styrene containing 105 g of polybutadiene dissolved therein and 1.5 g of TBPP. The gas present in the vacant space of the flask was replaced with a nitrogen gas. Subsequently, the resulting mixture was polymerized at 100° C. with stirring at 500 rpm for 4 hours (first-step polymerization). The amount of unreacted styrene was determined by means of gas chromatography (GLC), and the polymer conversion rate was found to be 40%.

Subsequently, the polymer thus obtained was transferred to a 5000 ml-capacity stainless steel autoclave, to which was added 3000 ml of an aqueous solution containing 0.2% of a mixture of partly saponified polyvinyl alcohol (saponification degree: 88%; polymerization degree: 2400)/ hydroxypropyl methyl cellulose (viscosity as a 2% aqueous solution at 20° C.: 100 cp)=1:1 dissolved therein. After the gas present in the vacant space of the autoclave was replaced with a nitrogen gas, the autoclave was hermetically sealed. Subsequently, the resulting mixture was heated continuously from 100 to 120° C. with stirring at 300 rpm over 4 hours to effect polymerization (second-step polymerization). After completion of polymerization, the resulting mixture was cooled, filtered and then dried to give a polymer as beads. Polymer conversion rate of styrene was 99%.

Graft efficiency of the bead-like polymer obtained was determined in the following manner:

From the polymer was collected 1 g of a sample, and the sample was subjected to extraction with methyl ethyl ketone employing a Soxhlet extractor for 24 hours so as to remove homopolystyrene. The residue was dried, and the weight of the dried residue was measured (A).

Graft efficiency was calculated employing the following expression:

Graft efficiency (%)=(A−amount of polybutadiene used)×100/ amount of polybutadiene used Thus, the graft efficiency was calculated to be 59%. The number average molecular weight and weight average molecular weight of polystyrene extracted with methyl ethyl ketone was found to be 182000 and 466000 respectively.

Comparative Example 9

The second-step polymerization was carried out in the same manner as in Example 15, except that 1.5 g of TBPP employed in Example 15 was replaced with 1.5 g of BBCP. The polymer conversion rate of styrene was found to be 99%, and the graft efficiency was 43%. The number average molecular weight and weight average molecular weight of polystyrene extracted with methyl ethyl ketone were found to be 155000 and 361000 respectively.

Therefore, the present examples and embodiments are to be considered as illustrative and not restrictive, and the invention is not to be limited to the details given herein, but may be modified within the scope of the appended claims.

What is claimed is:

1. A polyfunctional peroxide represented by the following general formula (2):

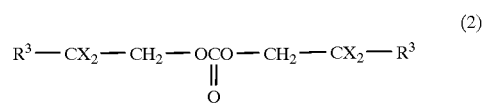

wherein $R^3$ represents a linear alkyl group having 1 to 3 carbon atoms; and X represents a group:

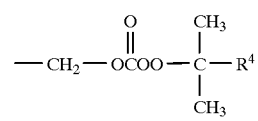

(wherein $R^4$ represents a linear or branched alkyl group having 1 to 5 carbon atoms).

2. The polyfunctional peroxide represented by the general formula (2) according to claim 1, wherein $R^3$ represents an ethyl group and $R^4$ contained in X represents a methyl group.

3. The polyfunctional peroxide represented by the general formula (2) according to claim 2, which is selected from the group consisting of di(2,2-bis(t-butylperoxycarbonyloxymethyl)butyl) carbonate and di(2,2-bis(1,1-dimethylbutylperoxycarbonyloxymethyl) butyl) carbonate.

* * * * *

UNITED STATES PATENT AND TRADEMARK OFFICE
CERTIFICATE OF CORRECTION

PATENT NO. : 5,973,181

DATED : Oct. 26, 1999

INVENTOR(S) : Hideyo Ishigaki et al

It is certified that error appears in the above-identified patent and that said Letters Patent is hereby corrected as shown below:

On the title page, item [73], Assignee "Nof Corporation" should be indicated.

Signed and Sealed this

Twenty-seventh Day of June, 2000

*Attest:*

Q. TODD DICKINSON

*Attesting Officer*      *Director of Patents and Trademarks*